United States Patent [19]

Dickhudt

[11] 4,383,532

[45] May 17, 1983

[54] EPIDURAL LEAD ADVANCER

[75] Inventor: Eugene A. Dickhudt, New Brighton, Minn.

[73] Assignee: Medtronic, Inc., Minneapolis, Minn.

[21] Appl. No.: 196,636

[22] Filed: Oct. 14, 1980

[51] Int. Cl.$^3$ .............................................. A61N 1/04
[52] U.S. Cl. ................................................ 128/419 P
[58] Field of Search ............... 128/657, 772, 783, 784, 128/785, 786, 419 P, 214.4

[56] References Cited

U.S. PATENT DOCUMENTS

| 2,129,391 | 9/1938 | Wappler | 128/6 |
| 3,838,688 | 10/1974 | May et al. | 128/214.4 |
| 3,847,140 | 11/1974 | Ayglla | 128/772 |
| 4,235,246 | 11/1980 | Weiss | 128/785 |

Primary Examiner—William E. Kamm
Attorney, Agent, or Firm—Merchant, Gould, Smith, Edell, Welter & Schmidt

[57] ABSTRACT

Surgical apparatus for propelling an epidural electrode (22) in an epidural needle (29), including a frame (41) having opposite inlet and outlet apertures for enabling axial passage of the electrode therethrough along a first axis of the frame, a pair of rollers (54, 57) mounted for rotation in the frame about further parallel axes orthogonal to the first axis, the rollers being configured and positioned to laterally engage the electrode therebetween, a driving interconnection (55, 60) between the rollers for simultaneous rotation about their axes in opposite directions to cause linear movement of the electrode along the first axis, disconnectable braking member (62) for opposing the rotation of said rollers while an electrode is being advanced and for allowing said rollers to rotate freely while the frame is being removed from an electrode, and an actuator (61) extending beyond the frame for causing rotation of the rollers. The frame may be configured (170) or cut to facilitate its removal from the needle by spreading or fracture, and an elastic band (174) may surround the frame to oppose unintended fracture.

12 Claims, 6 Drawing Figures

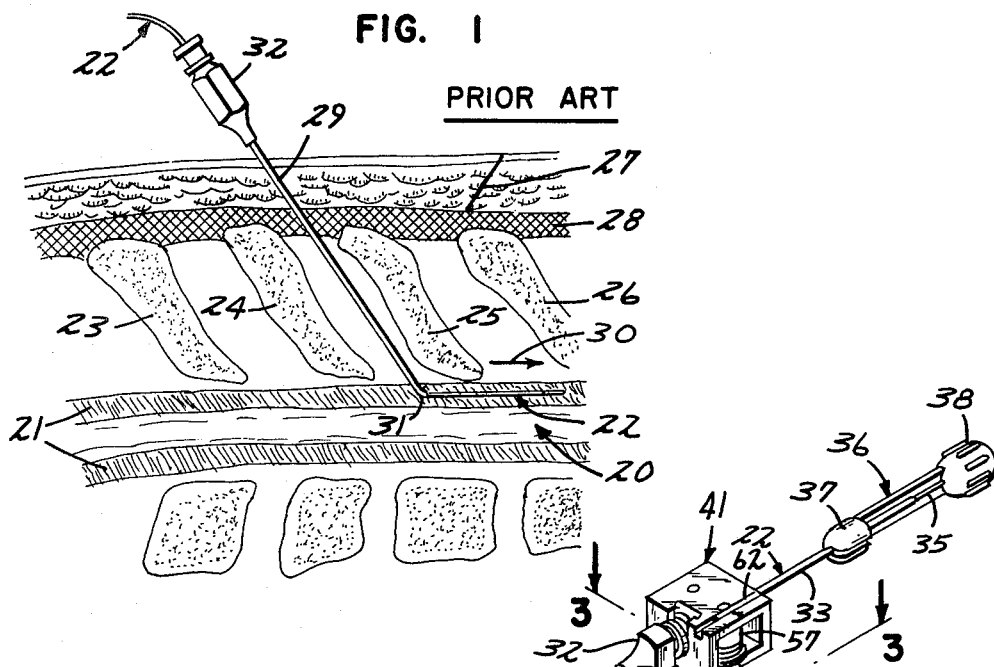
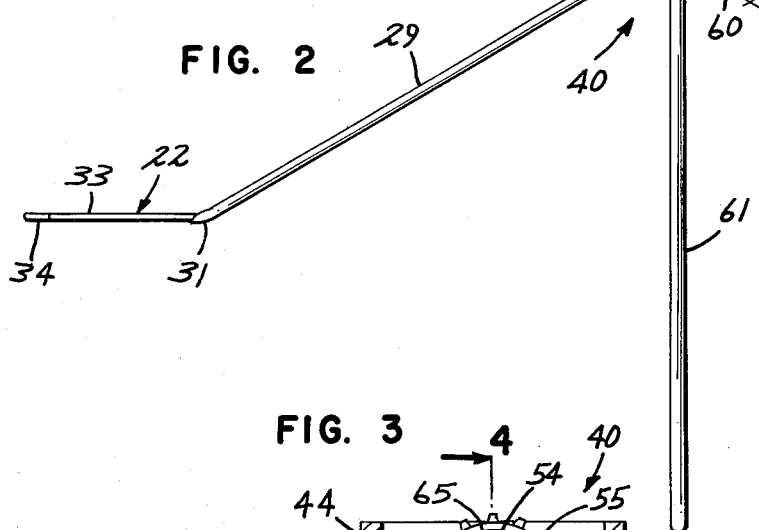
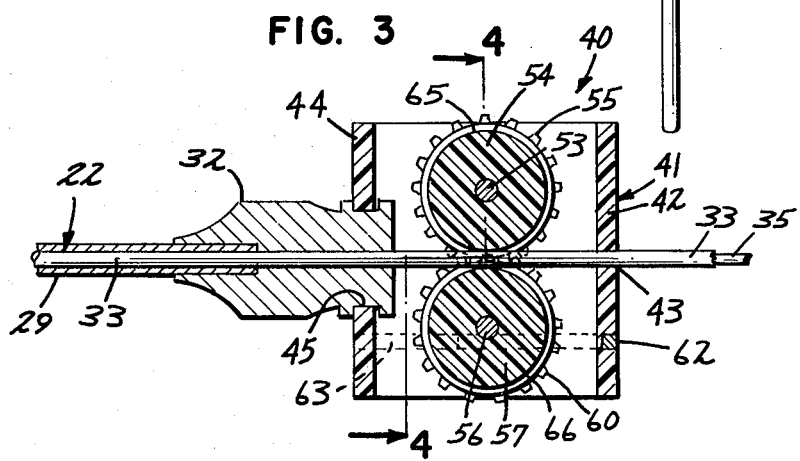

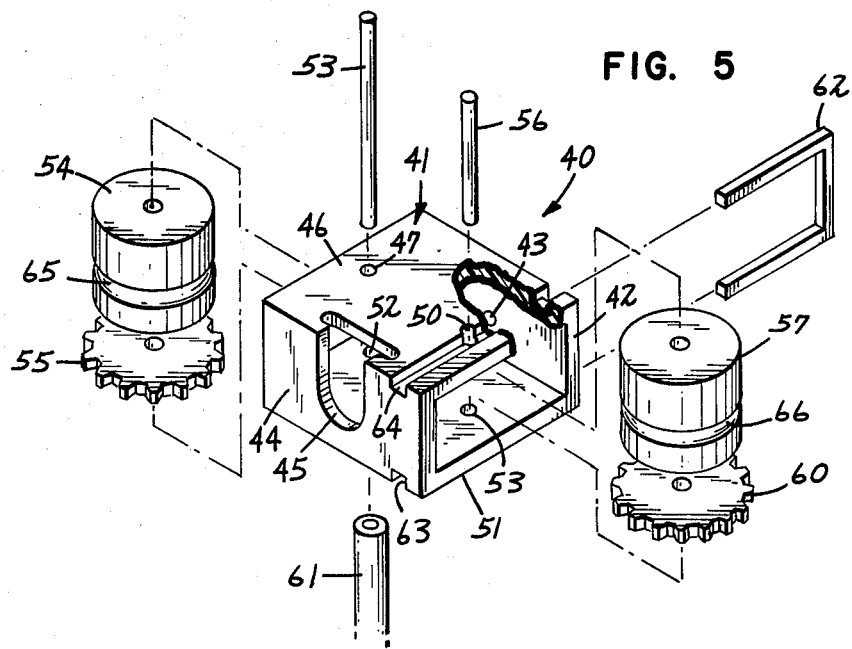
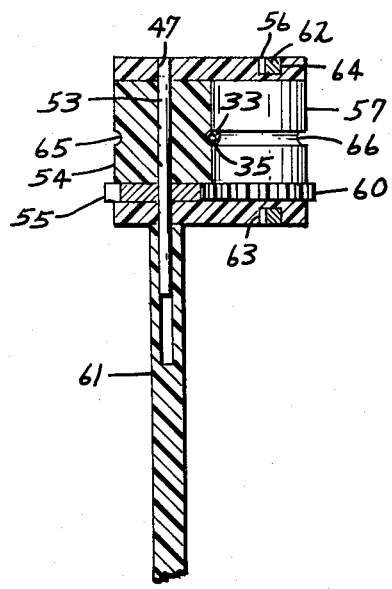
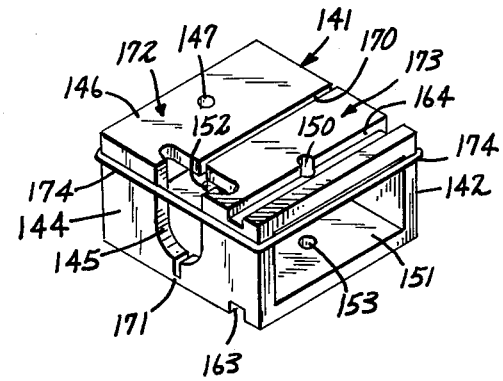

EPIDURAL LEAD ADVANCER

TECHNICAL FIELD

This invention relates to the field of surgery, and particularly to a method and apparatus for facilitating the insertion of epidural electrodes in the treatment of patients by spinal cord stimulation.

BACKGROUND OF THE INVENTION

A known technique for the management of chronic intractable pain of the trunk and limbs is the application of pulsed electrical stimulation through nerve structures in the dorsal aspect of the spinal cord. Spinal cord stimulation may be used either as a sole mitigating agent or as an adjunct to other modes of therapy.

The operative procedure involved comprises inserting a flexible electrode into the patient's epidural space, by passing it between two selected vertebrae and then advancing it under fluoroscopic observation until its end reaches the appropriate spinal level. Use is made of an epidural needle to guide the electrode past the bony structure and direct it properly into and along the epidural space.

An epidural lead or electrode is of necessity an elongated, highly flexible object, and difficulty is frequently encountered in advancing the electrode to its desired site. The procedure has the disadvantage that in order to advance the electrode the surgeon's hands must be in the fluroscopic field and hence subject to X-ray exposure. For the surgeon who frequently performs such electrode implant procedures, this involves undesirable repeated exposure to X-rays.

BRIEF SUMMARY OF THE INVENTION

The present invention comprises an instrument for association with an epidural needle to facilitate advance of a lead or electrode therethrough, while at the same time enabling the surgeon to perform the necessary manual operations at a site outside the X-ray field. This is accomplished by providing a frame containing a pair of rollers which engage the electrode laterally, the frame being removably securable to an epidural needle and having a handle, for causing roller rotation, which is long enough to extend out of the X-ray field. One embodiment of the invention is especially designed to simplify removal from the needle after use with minimum danger of disturbing the implanted electrode.

Various advantages and features of novelty which characterize the invention are pointed out with particularity in the claims annexed hereto and forming a part hereof. However, for a better understanding of the invention, its advantages, and objects attained by its use, reference should be had to the drawing which forms a further part hereof, and to the accompanying descriptive matter, in which there are illustrated and described certain preferred embodiments of the invention.

BRIEF DESCRIPTION OF THE DRAWING

In the drawing, in which like reference numerals indicate corresponding parts throughout the several views, FIG. 1 is a schematic view illustrative of a prior art operative procedure of implanting an epidural electrode;

FIG. 2 is a view in perspective of an instrument embodying the invention;

FIG. 3 is a view to a larger scale in section along the line 3—3 of FIG. 2;

FIG. 4 is a sectional view of the instrument along the broken line 4—4 of FIG. 3;

FIG. 5 is an exploded view of a portion of the invention; and

FIG. 6 is a fragmentary view showing a second embodiment of the invention.

DESCRIPTION OF THE PREFERRED EMBODIMENTS

Attention is first directed to FIG. 1 in which the spinal cord of a patient is indicated by reference numeral 20. The spinal cord is surrounded by the epidural space 21 along which a stimulation electrode or lead 22 is to be advanced to the appropriate spinal site for stimulation. Vertebrae are shown at 23, 24, 25, and 26. An incision 27 has been made to the depth of the subcutaneous fascia 28, and an epidural needle 29 has been inserted between vertebrae 24 and 25, through which an electrode 22 has been fed and is being advanced through the epidural space, in the direction of arrow 30, to a desired location. Needle 29 has a bend 31 at its outer end, to deflect the electrode along the epidural space in a desired direction.

Advancement of the electrode is effected in FIG. 1 by grasping the mounting flange 32 of the needle and feeding lead 22 into the needle. Inspection of FIG. 1 willll make it clear that manually advancing such a flexible elongated element as lead 22 into and through needle 29 can present considerable mechanical difficulty, and also will require the surgeon's hands to be close to flange 32 and hence in the X-ray field which is necessarily present if the procedure is to be properly monitored. This can lead to undesirable repeated exposure to X-rays for a surgeon who frequently performs such procedures. To avoid these problems, the invention comprises an advancer 40, designed to be removably secured to flange 32 of needle 29, by which the electrode can be reliably and conveniently fed into the needle by rotating a handle outside the X-ray field.

As seen in FIG. 2, an electrode or lead 22 comprises a very flexible coil 33 of very fine wire having a short solid tip 34 at one end and surrounding a stylet 35 of solid but still quite flexible wire. A handle 36 includes a clevis 37 to secure one end of coil 33, stylet 35 continuing to a knob 38 to facilitate electrical connections. Handle 36 is of appreciable length to enable a surgeon to keep his hands out of the X-ray field on the patient's back.

FIGS. 2–5 show that advancer 40 comprises a frame 41, conveniently of plastic, having the general form of a short tube of rectangular cross section. A first wall 42 of the frame has an aperture 43 sized to pass electrode 22, and a second, opposite wall 44 has a larger aperture 45 in which flange 32 of needle 29 may be removably secured coaxial with aperture 43. Flange 32 is non-circular so that it does not rotate in aperture 45. A third wall 46 has a pair of pivot holes 47, 50, and a fourth wall 51 has a second pair of pivot holes 52, 53 coaxial with the holes of the first pair.

A first pivot pin 53 passes in pivotal relation through apertures 47 and 52 to extend beyond wall 51. A first roller 54 is press fit on pin 53, and includes a pinion 55 which may be integral with the roller if desired. A second pivot pin 56 passes in pivotal relation through apertures 50 and 53, and a second roller 57 is press fit on pin 56 and likewise includes a pinion 60. Pins 53 and 56 have parallel axes, and are spaced to enable proper engagement between pinions 55 and 60. An extensional handle 61 is friction fit on shaft 53 outside of frame 41, and serves as the actuation member for advancing the lead. Specifically, the arrangement is such that rotation of handle 61 causes rotation of roller 53 in frame 41, so that by reason of pinions 55 and 60 roller 57 is also driven. Under some conditions pinions 55 and 60 may be omitted, only roller 54 being driven by handle 61.

A U-shaped spring 62 sliding in grooves 63 and 64 in frame 41 bears sideways against the ends of pin 56 to give a braking effect.

Rollers 54 and 57 are located on opposite sides of the axis of apertures 43 and 45, and are configured with grooves 65 and 66 respectively, of such location and depth as to laterally engage an electrode 22 passing between them and to advance it or withdraw it axially depending on the direction of rotation of the rollers. This can be done while the user holds handles 36 and 61 at sites outside the X-ray field. The procedure is facilitated by the fact that needle 29 when inserted in the patient's spine is quite rigidly held in place by anatomical structures not specifically shown in FIG. 1.

FIG. 6 shows a modification of the invention which has some practical advantages. Parts identical with those in FIG. 5 are given the same reference numerals in the 100 series. Frame 141 is also in the form of a tube of rectangular cross-section. Wall 142 is provided with an aperture, not shown, like aperture 43 of FIG. 5. Wall 124 has aperture 145 to receive the needle flange in non-rotating relationship. Wall 146 has apertures 147 and 150, and wall 151 has apertures 152 and 153, to receive the pivotal pins and rollers as before. The difference between this frame and that of FIG. 5 is that the frame is divided almost completely in half by a cut 170 which defines a plane passing through the axis of apertures 143 and 145 and parallel to the pivot pin axes. The cut completely severs wall 146, and severs all of walls 142, 144, and 151 except a very thin portion which remains as an integral hinge 171 between portions 172 and 173 of the frame. An elastic band 174 surrounds frame 141 above the axis of apertures 143 and 145, to prevent the hinge from being inadvertently broken: it may be removed temporarily when a needle 29 is to be inserted into aperture 145.

OPERATION

To use the instrument, a patient is prepared, the incision 27 is made, the fluoroscope is positioned, and a needle 31 is inserted between the appropriate vertebrae until its end 31 enters the patient's epidural space. Advancer 40 of FIGS. 2–5 is now positioned so that flange 32 of needle 29 enters aperture 45 and snaps in place: needle 29 may now be directed and rotated by manipulation of handle 61. An assembled electrode 22, stylet 35 and handle 36 is now fed, solid end 34 first, through aperture 43, between rollers 54 and 57, through flange 32 in aperture 45 and along needle 29 until it appears at bend 31. Unless deliberately manipulated, needle 29 retains its position, and by use of handle 61 the gradual feeding of the electrode through the needle and into the epidural space is accomplished without exposure of the surgeon to the X-ray field.

When tip 34 has reached a desired site, the electrode is removed from handle 36, and frame 41 is carefully removed from needle flange 32, fluoroscopic monitoring being maintained to be sure that the electrode is not disturbed. Now needle 29 is withdrawn from the patient leaving the electrode behind, the stylet is withdrawn from the coil, and the wound is closed by appropriate measures, the electrode remaining implanted in the patient for spinal cord stimulation as the symptoms dictate.

The operation of the invention using the embodiment of FIG. 6 is the same as described above, except that removal of frame 141 after the lead has been advanced is simplified. The elastic band 174 is cut and the frame is broken or simply spread along the line of hinge 171, allowing removal with almost no reactive forces on needle 29 which might otherwise tend to disturb it, the advancer being discarded if broken or reused with another elastic band if simply spread.

From the foregoing it will be clear that the invention comprises an adjunct instrument for use in implanting spinal cord stimulation electrodes in the epidural spaces of patients, with added convenience and minimum likelihood of electrode damage during the operation, and with removal of the surgeon's hands from the X-ray field.

What is claimed is:

1. Apparatus for advancing or withdrawing an epidural electrode comprising, in combination:
   a frame having opposite inlet and outlet apertures for enabling axial passage of the electrode therethrough along a first axis of the frame;
   a pair of rollers mounted for rotation in said frame about further parallel axes orthogonal to said first axis, said rollers being configured and positioned to laterally engage the electrodes therebetween;
   disconnectable braking means for opposing the rotation of said rollers; while an electrode is being advanced and for allowing said rollers to rotate freely while the frame is being removed from an electrode; and
   actuation means extending beyond said frame for causing rotation of at least one of said rollers.

2. Apparatus according to claim 1 further including means for removably mounting an epidural needle in said outlet aperture close to said rollers to guide said electrode after it leaves said rollers.

3. Apparatus according to claim 1 wherein said rollers have grooves in their surfaces for engaging said epidural electrode.

4. Apparatus according to claim 1 in which the interconnecting means comprises a pair of intermeshing pinions rotatable about said further axes integrally with said rollers and in which said actuation means comprises a handle connected to one of said rollers.

5. Apparatus according to claim 1 in which said one of said rollers includes a shaft pivoted in said frame and said actuation means includes a shaft secured thereto.

6. Apparatus according to claim 1 in which said frame is almost severed by a cut or gap in a plane parallel to said axes of said rollers and containing said first axis, to enable said frame to be spread for easy separation from said needle.

7. Apparatus according to claim 1 further including resilient means surrounding said frame generally in a plane perpendicular to said cut, to normally oppose fracture of said frame.

8. Apparatus according to claim 1 wherein said braking means comprises a U-shaped spring slidably mounted around said frame for applying a frictional breaking force to at least one of said rollers.

9. Apparatus according to claim 1 wherein said rollers are interconnected for simultaneous rotation about their axes in opposite directions, to cause linear movement of said electrode along said first axes.

10. Apparatus according to claim 1 wherein a stylet is removably attached to one end of the electrode for manipulating the electrode outside the X-ray field.

11. Apparatus for propelling an epidural electrode axially through an X-ray field comprising, in combination:

a pair of rollers grooved and positioned to jointly engage said electrode laterally, whereby rotation of said rollers accompanies movement of an electrode engaged by said grooves along its axes;

disengagable braking means for opposing the rotation of said rollers;

means mounting said rollers adjacent an epidural needle in the X-ray field so that said electrode as it leaves said rollers is aligned with the bore of said needle;

and manually actuable means extending beyond said field for causing rotation of at least one of said rollers.

12. Apparatus according to claim 11 wherein said mounting means includes a housing, said housing having a cut or gap part way through to facilitate separation of the propelling apparatus from the electrode by spreading of the housing.

* * * * *